United States Patent [19]

Rice et al.

[11] Patent Number: 5,663,466

[45] Date of Patent: Sep. 2, 1997

[54] MIXED PHASE BENZENE SATURATION WITH CONTROLLED HYDROGEN ADDITION

[75] Inventors: Lynn H. Rice, Palatine; Donald H. Bell, Mt. Prospect, both of Ill.

[73] Assignee: UOP, Des Plaines, Ill.

[21] Appl. No.: 351,963

[22] Filed: Dec. 8, 1994

Related U.S. Application Data

[63] Continuation-in-part of Ser. No. 138,720, Oct. 18, 1993, abandoned, which is a continuation of Ser. No. 985,661, Dec. 4, 1992, abandoned.

[51] Int. Cl.$^6$ .............................. C07C 5/10; C07C 5/22
[52] U.S. Cl. .................... 585/253; 585/266; 585/314
[58] Field of Search ............................. 585/253, 258, 585/266, 314, 734, 737

[56] References Cited

U.S. PATENT DOCUMENTS

5,003,118  3/1991  Low et al. ............................. 585/253

*Primary Examiner*—Glenn A. Caldarola
*Assistant Examiner*—Bekir L. Yildirim
*Attorney, Agent, or Firm*—Thomas K. McBride; John G. Tolomei

[57] ABSTRACT

A process for saturating benzene in a stream containing hydrocarbons and benzene maintains the benzene saturation reactor in a mixed phase at specific conditions to recover a saturation reactor effluent having a low benzene concentration and a reduced temperature. The benzene saturation reactor operates in a mixed phase without a hydrogen recycle and provides a saturated benzene effluent having less than 2 mol % benzene when operated at an effluent temperature of between 480° F. and 600° F. The discovered temperature range is relatively high and constant for feeds containing a substantial mount of benzene, despite changes in reaction zone pressure and reaction zone liquid LHSV.

21 Claims, 4 Drawing Sheets

MIXED PHASE BENZENE SATURATION WITH CONTROLLED HYDROGEN ADDITION

CROSS REFERENCE TO RELATED APPLICATIONS

This application is a continuation-in-part of U.S. Ser. No. 08/138,720, filed Oct. 18, 1993, now abandoned, which is a continuation of U.S. Ser. No. 985,661, filed Dec. 4, 1992, now abandoned.

FIELD OF THE INVENTION

This invention relates generally to the saturation of benzene. This invention relates more specifically to saturation of benzene and the control of hydrogen in the saturation of benzene.

DESCRIPTION OF THE PRIOR ART

Recent concerns about volatility and toxicity of hydrocarbon fuel and the resultant environment damage has prompted legislation that will limit the content and composition of aromatic hydrocarbons in such fuels. Many of these limitations relate specifically to benzene which, due to its toxicity, will be substantially eliminated from the gasoline pool. These new fuels are generally referred to as reformulated gasolines. New requirements for reformulated gasoline have profound impacts on the operation of refinery processes for producing high octane fuels. Reformulated gasoline requirements impose limitations on gasoline end points, benzene as well as total aromatics, and reid vapor pressure (RVP).

Benzene reduction will disrupt the current operation methods of several hydrocarbon processes that produce high octane fuel. Benzene reduction poses some of the most severe problems for the operation of catalytic reformers that have been relied on to raise the octane of unleaded fuels. Reformers that were typically operated at high severity to produce high octane benzene and aromatic hydrocarbons must now be operated to eliminate benzene and reduce aromatics. Reforming converts the $C_6$ and heavier hydrocarbons to aromatic compounds. Octane improvement is also obtained by catalytically isomerizing the paraffinic hydrocarbons to rearrange the structure of the paraffinic hydrocarbons into branch-chained paraffins such as normal $C_5$ hydrocarbons which are not readily converted into aromatics. Although the non-cyclic $C_6$ and heavier hydrocarbons can be upgraded into aromatics through dehydrocyclization, the conversion of $C_6$'s to aromatics creates higher density species and increases gas yields with both effects leading to a reduction in liquid volume yields. Therefore, it is preferable to charge the non-cyclic $C_6$ paraffins to an isomerization unit to obtain $C_6$ isoparaffin hydrocarbons. Consequently, octane upgrading commonly uses isomerization to convert normal $C_6$ and lighter boiling hydrocarbons and reforming to convert $C_6$ cycloparaffins and higher boiling hydrocarbons. However, both reforming and isomerization processes streams will require treatments for benzene elimination.

Elimination of benzene can be accomplished by removing benzene or benzene precursors from hydrocarbons prior to hydrocarbon conversion processes or removing benzene from the product stream by saturation, separation or conversion. Methods for eliminating benzene from a reforming effluent include direct saturation or saturation through isomerization. It is well known to eliminate benzene by direct saturation of product or feed streams such as an isomerization zone feed. U.S. Pat. No. 5,003,118 teaches a process for the directly saturating benzene in a benzene saturation reactor and passing the remainder of the stream as feed to an isomerization zone. The benzene contribution from the reformate portion of the gasoline pool can also be decreased or eliminated by altering the operation of the reforming section. There are a variety of ways in which the operation of the refining section may be altered to reduce the reformate benzene concentration. Changing the cut point of the naphtha feed split between the reforming and isomerization zones from 180° to 200° F. will remove benzene, cyclohexane and methylcyclopentane from the reformer feed. Benzene can alternately also be removed from the reformate product by splitting the reformate into a heavy fraction and a light fraction that contains the majority of the benzene. Practicing either method will put a large quantity of benzene into the feed to other processing units, particularly the isomerization zone. Therefore, it is still necessary to have an efficient and cost effective means for removing benzene from feeds.

The saturation of benzene for an isomerization process imposes several costs and process drawbacks. Where a saturation effluent from a benzene saturation reactor passes directly to isomerization reactors, the effluent must be brought to the isomerization reactor pressure. In addition for water sensitive catalysts, the hydrogen used in the benzene saturation must also undergo drying to keep water out of the feed to the isomerization reactors. When the concentration of benzene that requires isomerization increases, additional drying and compressor cost become significant due to the high relative hydrogen requirements to satisfy the stoichiometric requirements for benzene saturation. In addition, the heat integration important to isomerization reactors does not permit full recovery of the heat of reaction released in the benzene saturation reactor. Accordingly, the direct coupling of benzene saturation with the isomerization reactors does not provide heat utilization benefits.

It is an object of this invention to provide a process that will more efficiently and more cost effectively saturate benzene in hydrocarbon feedstreams and effluent streams.

It is a particular object of this invention to provide a benzene saturation process that improves the efficiency and cost effectiveness of saturating benzene in a feed to an isomerization reaction zone.

BRIEF DESCRIPTION OF THE INVENTION

This invention is a process for saturating benzene in a stream containing hydrocarbons and benzene that maintains the benzene saturation reactor in a mixed phase at specific operating conditions to recover a saturation reactor effluent having a low benzene concentration. It has been found that a benzene saturation reactor operating in a mixed phase without a hydrogen recycle can provide a saturated benzene effluent having less than 2 mol % benzene when operated with an effluent temperature maintained between 480° F. and 600° F. Higher operating temperatures for the benzene saturation reactor have been avoided since the saturation reactor effluent often serves as the input for isomerization zones which typically operate at relatively low temperatures. Higher temperatures also tend to increase metallurgy requirements and could raise the mount of benzene in the product. In addition lower temperatures were generally found to be most desirable for the hydrogenation reaction since they minimize unwanted disproportionation and cracking reactions that reduce the yield of the isomerization zone product. Surprisingly, the discovered temperature range is relatively high and constant for feeds containing a substantial amount of benzene, despite changes in reaction zone pressure and reaction zone liquid hourly space velocity (LHSV).

With the simple hydrogen control and operating conditions, it is possible to maintain very low hydrogen levels in the benzene saturation reactor and the effluent from the benzene saturation zone. By this method, it is possible to keep a hydrogen to hydrocarbon ratio of less than 0.02 in the effluent from the benzene saturation reaction zone. This very low level of excess hydrogen in the benzene saturation zone means that essentially all of the hydrogen entering the benzene saturation zone is used in the saturation reaction. It is possible to operate the process of this invention in a manner such that the effluent from the benzene saturation reaction zone maintains hydrogen concentrations of less than 1 mol %. These low hydrogen concentrations have the overall advantage of conserving hydrogen in the benzene saturation process. The conservation of hydrogen is particularly useful in today's reforming processes where hydrogen demands are on the rise for other processes such as hydrotreatment and desulfurization. The reduction of hydrogen to very low levels in the benzene saturation reactor effluent also has the advantage of simplifying required facilities for the separation of the benzene saturation effluent.

Accordingly, in one embodiment this invention is a process for the saturation of benzene. The process includes passing a feedstream comprising at least one of a $C_4$ to $C_7$ paraffinic hydrocarbon and benzene into admixture with a hydrogen containing stream in an mount regulated by a flow controller to produce a combined feed. The process contacts the combined feed with a benzene saturation catalyst in a benzene saturation zone at benzene saturation conditions including mixed phase conditions and withdraws a saturation effluent stream from the benzene saturation zone at a temperature of from 480° F. to 600° F. The benzene saturation effluent contains not more than 2 mol % benzene. In response to the mount of hydrogen in the saturation effluent stream the process varies the amount of the hydrogen stream admixed with the feed to the saturation reactor.

In a yet further embodiment, this invention is a process for the saturation of benzene and the isomerization of hydrocarbons comprising passing a feedstream comprising at least one of $C_5$ and $C_6$ paraffinic hydrocarbons and benzene to a guard bed for the removal of sulfur; splitting a hydrogen rich stream into a first hydrogen stream and a second hydrogen stream; drying the first hydrogen stream in a drier to produce a dried hydrogen stream; admixing the feedstream from the guard bed with the second hydrogen stream in an amount regulated by a flow controller to produce a combined feed; contacting the combined feed with a hydrogenation catalyst in a benzene saturation zone with a benzene saturation catalyst at benzene saturation conditions including mixed phase conditions; withdrawing a saturation effluent stream from the benzene saturation zone at a temperature of from 480° F. and 600° F., the benzene saturation effluent containing not more than 2 mol % benzene; cooling the saturation zone effluent stream and passing the saturation zone effluent stream to a receiver; maintaining the receiver at the bubble point of the saturation zone effluent stream and sensing the pressure in the receiver; adjusting the amount of the second hydrogen stream admixed with effluent of the guard bed by the flow controller in response to the pressure in the receiver; recovering a saturated effluent stream from the receiver, drying the saturated effluent stream and combining the dried saturated effluent stream with the first hydrogen stream to produce an isomerization zone feed stream; passing the isomerization zone feed stream to an isomerization reactor and contacting the isomerization zone feed stream with an isomerization catalyst at isomerization conditions; and, recovering an isomerization zone product stream from the isomerization reaction zone.

This invention is of particular benefit to processes that require benzene saturation of a feedstream upstream of process reactors that are sensitive to water or other contaminants commonly found in refinery hydrogen streams. For example, in the case of an isomerization reaction zone that uses a water sensitive isomerization catalyst, all of the entering reactant streams must undergo drying to remove water to levels of less than 0.1 ppm. The feedstream to such an isomerization reaction zone can typically contain in excess of 30 vol. % benzene. The amount of hydrogen required for saturating these high levels of benzene exceeds the amount of hydrogen required in the isomerization reaction zone by a ratio of 5. The process eliminates the need for drying excess hydrogen that passes to the isomerization reactors without requiring the addition of a hydrogen separator. The process also has the advantage of reducing the heat input to the saturation effluent by operating at mixed phase conditions so that the latent heat effects from the vaporization of a portion of the feed absorbs a portion of the exothermic heat evolved from the saturation reaction. Thus the process when applied to isomerization can simplify hydrogen circulation, lower treatment costs, and reduce temperatures of effluent streams to those more favorable for the isomerization reactions.

Other embodiments, aspects and details of this invention are disclosed in the following detailed description of the invention.

DETAILED DESCRIPTION OF THE INVENTION

The advantages of this invention in obtaining a high benzene conversion with reduced heat generation is applicable to a variety of feedstreams. Suitable feedstocks for this invention will generally include $C_4$ plus hydrocarbons up to an end boiling point of about 250° C. (482° F.). The feedstocks that are used in this invention will typically include hydrocarbon fractions rich in $C_4$–$C_6$ normal paraffins. The term "rich" is defined to mean a stream having more than 50% of the mentioned component. In addition, the feedstock will include significant amounts of benzene. In order to realize the advantages of this invention, the concentration of benzene in the feedstock will usually at least equal 5 mol % and will normally be higher. Preferably, in order to obtain the benefits of this invention, the concentration of benzene will equal at least 10 mol % and more preferably at least 15 mol %. Accordingly, the benzene content of the feed will normally be in a range of from 10 to 25 mol %. There is no upper limit on the concentration of benzene. Where the saturation process of the invention is used in combination with an isomerization process, the maximum benzene content is dictated by the need to have sufficient paraffinic hydrocarbons present for the isomerization reaction. Other feed components will usually comprise $C_5$–$C_6$ cyclic and paraffinic hydrocarbons with normal and isohexane providing most of the paraffinic components.

The benzene saturation zone of this invention contacts the feed with a hydrogenation catalyst. The saturation zone will typically comprise a fixed bed of catalyst for promoting the hydrogenation of benzene. Suitable hydrogenation catalysts will provide a metallic function to promote hydrogen transfer without any substantial acid function that would lead to undesirable cracking. Preferred catalyst compositions will include platinum group, tin or cobalt and molybdenum metals on suitable refractory inorganic oxide supports such as alumina. The alumina is preferably an anhydrous gamma-alumina with a high degree of purity. The term platinum group metals refers to noble metals excluding silver and gold which are selected from the group consisting of platinum, palladium, germanium, ruthenium, rhodium, osmium, and iridium.

Such catalysts will provide satisfactory benzene saturation at the operating conditions of this invention. The operating conditions include temperatures of from 480° F. to 600° F., preferably from 500° F. to 550° F., pressures of from 300 to 700 psig, preferably from 400 to 500 psig, and a 1 to 20 liquid hourly space velocity (LHSV), preferably from 4 to 12.

A particularly preferred catalyst comprises a platinum metal on an alumina support. In its preferred form the alumina support will comprise spheres having a nominal diameter of about 1/16" and surface area of from about 160 to 200 m²/g with an apparent bulk density of from about 0.45 to 0.6. Platinum metal may be present on the catalyst in a concentration of from 0.1 to 1 wt % and preferably in a concentration of from 0.375 to 0.75 wt %.

The hydrogenation zone catalyst and, when present, the isomerization zone catalyst are often sulfur sensitive. Suitable guard beds or adsorptive separation processes may be used to reduce the sulfur concentration of the feedstock. Preferably the sulfur in the feed to the saturation zone will have a sulfur concentration of less than 0.1 ppm. The sulfur concentration to most isomerization zones should be reduced to less than 0.5 ppm.

As hereinafter described in more detail, when the process is used in combination with an isomerization zone, many of the possible isomerization zone catalysts suitable for use in this invention are highly sensitive to water and other contaminants. In order to keep the water content within acceptable levels for such catalysts, those portions of the feed that enter the isomerization zone, including any added hydrogen, pass through a drying zone. The drying zone for this purpose may be of any design that will reduce water content to 0.1 ppm or less. Suitable adsorption processes for this purpose are well known in the art.

A hydrogen stream is combined with the feedstock to provide hydrogen for hydrogenation in the saturation reactor and any downstream isomerization. The amount of hydrogen admixed with the feedstock varies widely. In the case of a combined isomerization zone, hydrogen in the isomerization zone alone can vary to produce anywhere from a 0.01 to a 10 hydrogen to hydrocarbon ratio in the isomerization zone effluent. Consumption of hydrogen in the saturation zone increases the required amount of hydrogen admixed with the feedstock. This process seeks to minimize the hydrogen to hydrocarbon ratio in the saturation zone. Therefore, hydrogen will usually be mixed with the feedstock in an amount sufficient to create a combined feed having a hydrogen to hydrocarbon ratio of from 0.1 to 1. Low hydrogen to hydrocarbon ratios in the combined feed are necessary to keep the system and equipment associated with the addition of hydrogen simple. At minimum, the hydrogen to hydrocarbon ratio must supply the stoichiometric requirements for the saturation reaction. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and any remaining aromatics, cracking and disproportionation. Due to the presence of the benzene saturation zone, little saturation of olefins and aromatics will occur in the isomerization zone. Nevertheless, hydrogen in excess of the stoichiometric amounts for the side reactions is maintained in the isomerization zone to provide good stability and conversion by compensating for variations in feedstream compositions that alter the stoichiometric hydrogen requirements and to prolong catalyst life by suppressing side reactions such as cracking and disproportionation. Side reactions left unchecked reduce conversion and lead to the formation of carbonaceous compounds, i.e, coke, that foul the catalyst. As a result, the effluent from the hydrogenation zone normally contained enough hydrogen to satisfy the hydrogen requirements for the isomerization zone.

It has been found to be advantageous to minimize the amount of hydrogen added to the isomerization zone feedstock. When the hydrogen to hydrocarbon ratio at the effluent of the isomerization zone exceeds about 0.05, it is not economically desirable to operate the isomerization process without the recovery and recycle of hydrogen to supply a portion of the hydrogen requirements. Facilities for the recovery of hydrogen from the effluent are needed to prevent the loss of product and feed components that can escape with the flashing of hydrogen from the isomerization zone effluent. These facilities add to the cost of the process and complicate the operation of the process. The isomerization zone can be operated with the effluent hydrogen to hydrocarbon ratio as low as 0.05 without adversely affecting conversion or catalyst stability. Accordingly, where possible, the addition of hydrogen to the isomerization zone feedstock will be kept to below an amount that will produce a hydrogen to hydrocarbon ratio in excess of 0.05 in the effluent from the isomerization zone.

When the hydrogen is added downstream of the feedstock treating section, the hydrogen stream also undergoes drying or other treatment necessary for the sustained operation of the isomerization zone. Typically, the amount of hydrogen added to the saturation feedstock was sufficient for both the requirements of the hydrogenation zone and the isomerization zone. The process disclosed herein reduces the amount of hydrogen that requires treatment for water removal by minimizing the amount of excess hydrogen that passes through the benzene saturation reactor. By the arrangement of this invention, hydrogen converted in the benzene saturation reactor does not require drying. The hydrogen concentration of the effluent from the saturation reactor is limited essentially to dissolved hydrogen levels. Dissolved hydrogen in the saturation effluent undergoes drying along with the rest of the isomerization feed hydrocarbons passing to the isomerization zone.

The saturation reaction zone produces an effluent with dissolved hydrogen levels by controlling the addition of hydrogen at or near stoichiometric requirements. Any suitable means for maintaining the hydrogen addition at or near stoichiometric requirements can be used. Suitable methods include on line analysis of benzene concentration in the input or effluent of the saturation zone with manual or automatic control of the hydrogen addition rate to the feedstream. In a preferred form, pressure monitoring of the hydrogen content of the benzene reaction zone effluent provides input for the automatic adjustment of the hydrogen addition rate to the benzene containing stream. Passing the benzene saturation zone effluent to a receiver maintained at the bubble point of the effluent stream allows monitoring of hydrogen partial pressure variations in the top of the receiver. As hydrogen partial pressure falls with hydrogen concentration, a pressure monitor senses a fall in pressure and ramps open a flow controller for the hydrogen stream. Conversely, as the hydrogen consumption falls with decreasing benzene concentration, hydrogen partial pressure rises triggering a closing of the hydrogen stream flow controller. Ordinarily the saturation effluent entering the receiver will be cooled to a temperature in a range of from 100° F. to 150° F. This method provides a simple direct means for automatic hydrogen control.

In a highly preferred embodiment saturated feed from the saturation zone enters the isomerization zone for the rearrangement of the paraffins contained therein from less highly branched hydrocarbons to more highly branched hydrocarbons. Furthermore, if there are any unsaturated compounds that enter the isomerization zone after passage through the hydrogenation zone, these residual amounts of unsaturated hydrocarbons will be quickly saturated in the isomerization zone. The isomerization zone uses a solid isomerization catalyst to promote the isomerization reaction. There are a number of different isomerization catalysts that can be used for this purpose. The two general classes of isomerization catalysts use a noble metal as a catalytic component. This noble metal, usually platinum, is utilized on a chlorided alumina support when incorporated into one general type of catalyst and for the other general type of catalyst the platinum is present on a crystalline alumina silicate support that is typically diluted with an inorganic binder. Preferably, the crystalline alumina type support is a zeolite support and more preferably a mordenite type zeolite. The zeolite type isomerization catalysts are well known and are described in detail in U.S. Pat. Nos. 3,442,794 and 3,836,597.

Although either type of catalyst may be used in this invention, the preferred catalyst is a high chloride catalyst on an alumina base that contains platinum. The alumina is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process.

The isomerization catalyst also contains a chloride component. The chloride component termed in the art "a combined chloride" is present in an amount from about 2 to about 10 wt. % based upon the dry support material. The use of chloride in amounts greater than 5 wt. % have been found to be the most beneficial for the isomerization process.

As mentioned previously many dehydrogenation and isomerization catalysts are sulfur sensitive. The presence of sulfur in the feedstock serves to temporarily deactivate platinum type catalysts by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst.

But looking at the chlorided isomerization catalysts, water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. As previously mentioned, the feedstock may be treated by any method that will remove water and sulfur compounds. Sulfur may be removed from the feedstock by hydrotreating. Adsorption processes for the removal of sulfur and water from hydrocarbon streams are also well known to those skilled in the art.

Operating conditions within the isomerization zone are selected to maximize the production of isoalkane product from the feed components. Temperatures within the reaction zone will usually range from about 40°260° C. (105°–500° F.). Lower reaction temperatures are preferred for purposes of isomerization conversion since they favor isoalkanes over normal alkanes in equilibrium mixtures. The isoalkane product recovery can be increased by opening some of the cyclohexane rings produced by the saturation of the benzene. However, if it is desired, maximizing ring opening usually requires temperatures in excess of those that are most favorable for the isomerization reaction from an equilibrium standpoint. For example, when the feed mixture is primarily $C_5$ and $C_6$ alkanes, temperatures in the range of 60°–160° C. are desired from a normal-isoalkane equilibrium standpoint, in order to achieve significant opening of $C_5$ and $C_6$ cyclic hydrocarbon ring, the preferred temperature range for this invention lies between 100°–200° C. When it is desired to also isomerize significant amounts of $C_4$ hydrocarbons, higher reaction temperatures are required to maintain catalyst activity. Thus, when the feed mixture contains significant portions of $C_4$–$C_6$ alkanes, the most suitable operating temperatures for ring opening and isoalkane equilibrium coincide and are in the range from 145°–225° C. The reaction zone may be maintained over a wide range of pressures. Pressure conditions in the isomerization of $C_4$–$C_6$ paraffins range from 7 barsg to 70 barsg. The feed rate to the reaction zone can also vary over a wide range. These conditions include liquid hourly space velocities ranging from 0.5 to 12 hr.$^{-1}$, however, space velocities between 0.5 and 3 hr.$^{-1}$ are preferred.

Operation of the reaction zone also requires the presence of a small amount of an organic chloride promoter. The organic chloride promoter serves to maintain a high level of active chloride on the catalyst as small amounts of chloride are continuously stripped off the catalyst by the hydrocarbon feed. The concentration of promoter in the reaction zone is usually maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there is no adverse effect from the presence of small amounts of hydrogen chloride.

A preferred manner of operating the isomerization process is in a two-reactor, reaction zone system. The catalyst used in the process can be distributed equally or in varying proportions between the two reactors. The use of two reaction zones permits a variation in the operating conditions between the two reaction zones to enhance isoalkane production. In this manner the final reactor stage may operate at temperature conditions that are more favorable for isoalkane equilibrium.

A typical isomerization process for use in this invention has two reaction zones. The combined feed is heat exchanged in an exchanger against the contents of the isomerization effluent from a second isomerization reactor. The heat exchange combined feed is further heat exchanged with the effluent from a first isomerization reactor. Whether operated with one or two reaction zones, the effluent of the isomerization process will enter separation facilities for the recovery of an isoalkane product. At minimum, the separation facilities divide the reaction zone effluent into a product stream comprising $C_5$ and heavier hydrocarbons and a gas stream which is made up of $C_3$ lighter hydrocarbons and hydrogen. Suitable designs for rectification columns and separator vessels to separate the isomerization zone effluent are well known to those skilled in the art.

Figure 1:
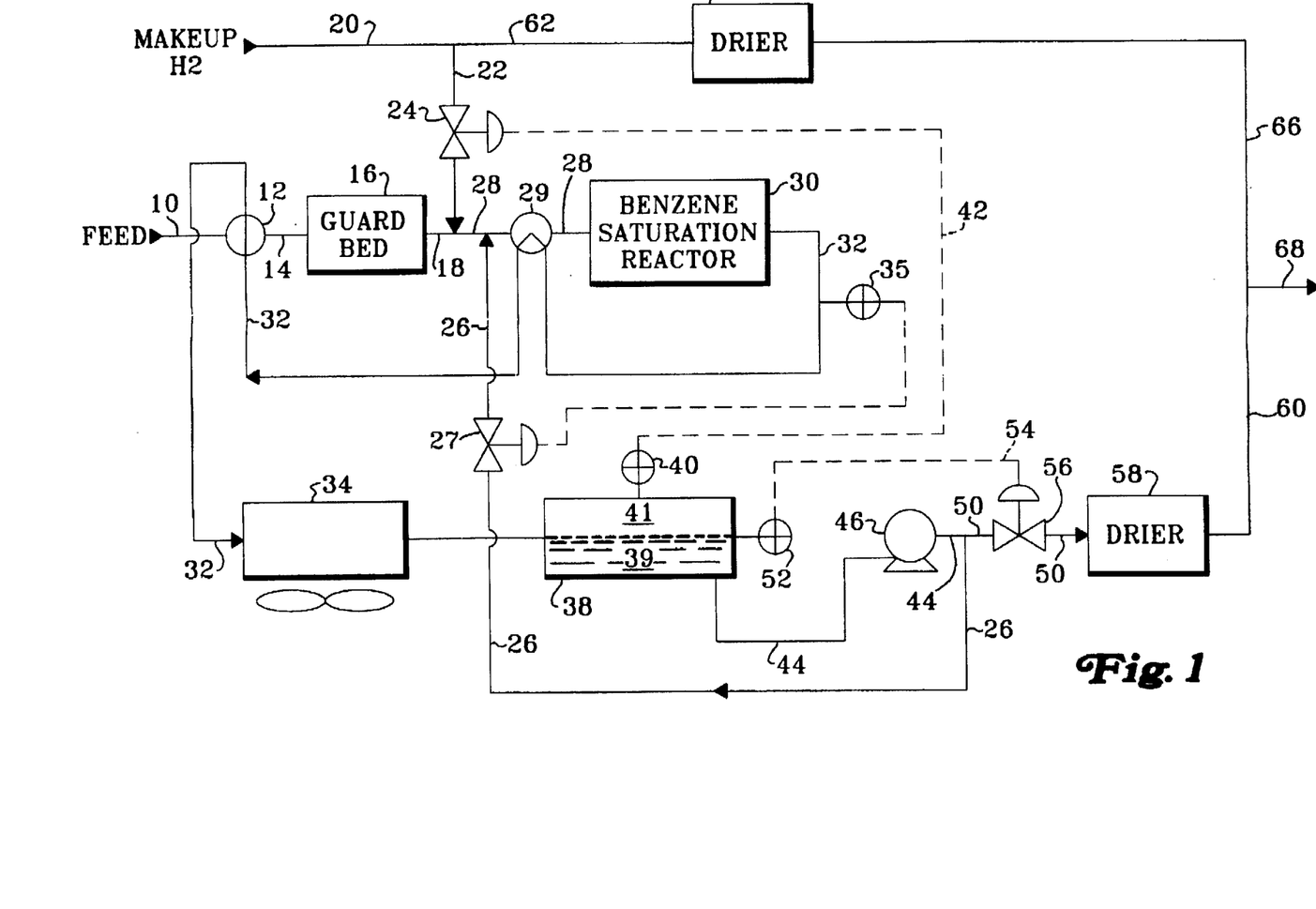
FIG. 1 shows a preferred arrangement for the benzene saturation process of this invention.

A basic arrangement for the processing equipment used in this invention can be readily understood by a review of the flow scheme presented in FIG. 1. FIG. 1 and this description makes no mention of many pumps, compressors, receivers, condensers, reboilers, instruments, and other well known items of processing equipment in order to simplify the explanation of the invention.

Looking then at the Figure, a feedstream comprising $C_4$ to $C_7$ paraffins along with benzene enters the process through a ling 10 and passes through a heat exchanger 12 to heat the feed before it enters a guard bed 16 via a line 14. Guard bed 16 consists of a nickel promoted adsorbent that removes sulfur and produces a relatively sulfur free feed that exits the guard bed via a line 18 and is admixed with hydrogen. The Figure shows the treatment of the feedstock upstream of the hydrogen addition point and the hydrogenation zone; however, the feedstock may be treated for any necessary contaminant removal at any point upstream of the saturation catalyst.

Make-up hydrogen enters the process through a line 20. A line 22 splits off hydrogen from line 20 at a rate regulated by a control valve 24. A line 62 carries the remainder of the hydrogen to a drier 64 that consists of at least two beds of adsorbent that remove water and produce a relatively dry hydrogen stream transported by line 66.

Line 28 passes the admixture of hydrogen and hydrocarbons into a heat exchanger 29 and then into a benzene saturation reactor 30. Benzene saturation reactor 30 contains a platinum catalyst on an alumina support that reduces the concentration of benzene in the feed stream to less than 2 mol %. Exothermic saturation of benzene typically provides the necessary heat input for the saturation reaction. The saturation zone effluent carried by a line 32 passes from the reactor through heat exchanger 29 to heat the saturation feed, heat exchanger 12 to provide heat for the sulfur guard bed and then passes into a cooler 34. A temperature recorder 33 senses the temperature of the effluent and when the effluent temperature exceeds a predetermined limit, lowers the temperature of the inlet stream to the saturation reactor by adding cooled saturation effluent at a rate regulated by a control valve 27.

From cooler 34, line 36 empties the saturation reactor effluent into a receiver 38. Vaporization of excess hydrogen in receiver 38 forms a liquid hydrocarbon rich phase 39 and a gaseous hydrogen rich phase 41. A pressure recorder controller 40 senses the pressure of hydrogen vapor in phase 41 and sends a signal 42 to control valve 24 to regulate the addition of hydrogen in the manner described herein.

A pump 46 withdraws the liquid phase 39 from the bottom of receiver 38 through line 44. Downstream of pump 46, line 26 withdraws cooled effluent as necessary for the previously described saturation reactor temperature control. In most operations, line 26 only finds intermittent use in the case of temporary temperature runaways and does not constantly withdraw effluent. After the junction of line 26, a line 50 removes the treated effluent from the benzene saturation portion of the process. A control valve 56 across line 50 regulates the rate of effluent discharge from the saturation process to maintain a liquid level in receiver 38. A liquid level indicator 52 provides input for setting the flow rate through valve 56. Valve 56 may respond automatically via a signal 54 generated by level indicator 52. Alternatively the valve 56 may be adjusted manually in response to data read from indicator 52 or other such monitoring devices. When valve 56 operates on manual control, receiver 38 is ordinarily sized larger to permit more variation in the liquid level of receiver 38.

FIG. 1 demonstrates the preferred form of this invention where the saturated effluent from line 50 passes to an isomerization zone. In the embodiment of FIG. 1 the saturation effluent from line 50 passes through a drier 58 for water removal. After water removal, line 68 receives the dried effluent 60 and the dried hydrogen from line 66 for passage to an isomerization reaction zone.

EXAMPLES

EXAMPLE 1

In order to more fully illustrate the process, the following example is presented to demonstrate the operation of the process utilizing the flow scheme of the Figure. This example is based in part on a computer simulation of the process and experience with operating saturation, isomerization and fractionation systems. All of the numbers identifying vessels and lines correspond to those given in FIG. 1.

A $C_5$ plus naphtha feed enters through line 10 and, after passage through heat exchanger 12 and guard bed 16, is combined with about 1200 lb/hr of hydrogen split from a hydrogen feed to produce about 139,000 lb/hr of combined feed having the relative composition given in Table 1 for line 18. The combined feed after additional heat exchange enters the saturation reactor at a pressure of about 480 psig, a temperature of about 360° F. and an LHSV of about 8. In the saturation reactor, the combined feed is contacted with a catalyst comprising about 0.75 wt % of a platinum metal on an alumina support. Contact of the combined feed with the catalyst produces a saturated feedstream that is withdrawn by line 32 at a temperature of about 500° F. and has the composition listed in Table 1.

The saturation reactor effluent enters receiver 38 at a temperature of about 100° F. after heat exchange in exchanger 29 and exchanger 12 and cooling in cooler 34. The gas and liquid phase is maintained in the receiver at a pressure of about 450 psig. Valve 56 responds to a signal from level indicator 52 to maintain a liquid level in receiver 38.

About 700 lbs per hour of dried hydrogen is admixed with the dried and cooled saturation effluent from drier 58 and line 60 to provide an isomerization zone feed having, except for the addition of hydrogen, the approximate composition given in Table 1 under line 32. Carbon tetrachloride is then added to the isomerization feedstream at a rate of 150 wt. ppm which then enters a two reactor train of the isomerization zone. The combined isomerization feed enters a first isomerization reactor at a temperature of about 355° F. passes from the first reactor to a second reactor at a temperature of about 285° F. The isomerization feed passes through both reactors at a pressure of about 480 psig and an LHSV of about 1. In the isomerization reactors the isomerization feed contacts an alumina catalyst having 0.25 wt % platinum and 5.5 wt % chloride which was prepared by vacuum impregnating an alumina base in a solution of chloroplatinic acid, 2% hydrochloric acid, and 3.5% nitric acid and a volume ratio of 9 parts solution to 10 parts base to obtain a peptized base material having a solution to base ratio of approximately 0.9. The preparation also included cold rolling the catalyst for approximately 1 hour followed by evaporation until dry. Afterward the catalyst was oxidized and the chloride content adjusted by contact with a 1 molar hydrochloric acid solution at 525° C. (975° F.) at a rate of 45 cc per hour for 2 hours. The catalyst was then reduced in electrolytic hydrogen at 565° C. (1050° F.) for 1 hour and was found to contain approximately 0.25 wt % platinum and approximately 1 wt % chloride. Impregnation of active chloride to a level of approximately 5.5 wt % was accomplished by sublimating aluminum chloride with hydrogen and contacting the catalyst with a sublimated aluminum chloride for approximately 45 minutes at 550° C. (1020° F.). The converted isomerization zone feed passes out of the reactor train at a temperature of about 225° F. and a pressure of about 450 psig to provide about 140,000 lb/hr of unstabilized product having the composition listed in Table 1 for the isomerization product.

This example demonstrates the ability of the process to obtain an essentially complete benzene saturation with mixed phase saturation conditions at the operating conditions of this invention.

TABLE 1

Relative Stream Composition (molar ratios)

| Component | Stream 18 | Stream 32 | Isomer. Product |
|---|---|---|---|
| hydrogen | 22.3 | 2.1 | 8.7 |
| $C_1$-$C_3$ | .6 | .7 | 3.3 |
| isobutane | 1.7 | 2.1 | 3.6 |
| normal butane | 3.6 | 4.5 | 4.9 |
| isopentane | 16.0 | 18.2 | 27.5 |
| normal pentane | 15.8 | 19.9 | .9 |
| cyclopentane | 1.3 | 1.6 | 1.0 |
| 2,2 dimethyl butane | .8 | 1.1 | 9.0 |
| 2,3 dimethyl butane | 1.4 | 1.7 | 3.1 |
| 2 methyl pentane | 7.7 | 9.6 | 10.3 |
| 3 methyl pentane | 4.9 | 6.2 | 5.5 |
| normal hexane | 9.8 | 12.3 | 3.5 |
| methyl cyclopentane | 3.6 | 4.5 | 4.4 |
| cyclohexane | 1.6 | 10.7 | 4.5 |
| benzene | 6.8 | — | — |
| $C_7$ and higher hydrocarbons | 2.2 | 2.8 | 1.3 |

EXAMPLE 2

In order to further demonstrate the range of operating temperatures that have been discovered to provide the benefits of this invention a series of experiments were run at different temperature, pressure and space velocity conditions. These experiments were run on a feed having the composition given in Table 2. The feed was contacted with a spherical platinum catalyst on an alumina support comprising spheres having a nominal diameter of about 1/16" and a surface area of from about 170 to 190 m²/g with an apparent bulk density of from about 0.50 to 0.55. The platinum metal was present on the catalyst in a concentration of about 0.75 wt %.

Figure 2:
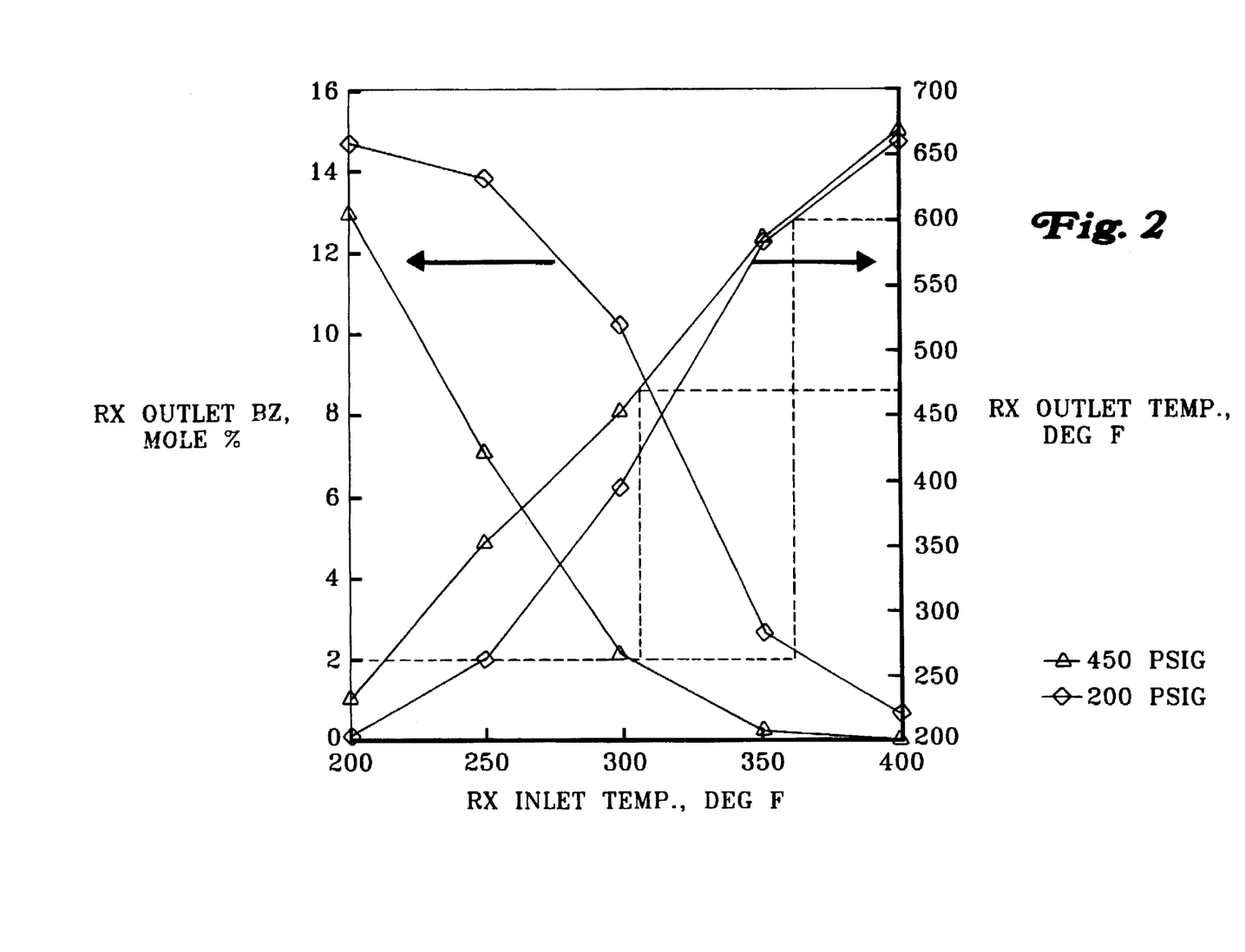
FIG. 2–4 are graphs showing the effect of reactor outlet temperature on the benzene concentration in the effluent resulting from variations in the reactor pressure, space velocity, and feedstream benzene concentration.
Figure 3:
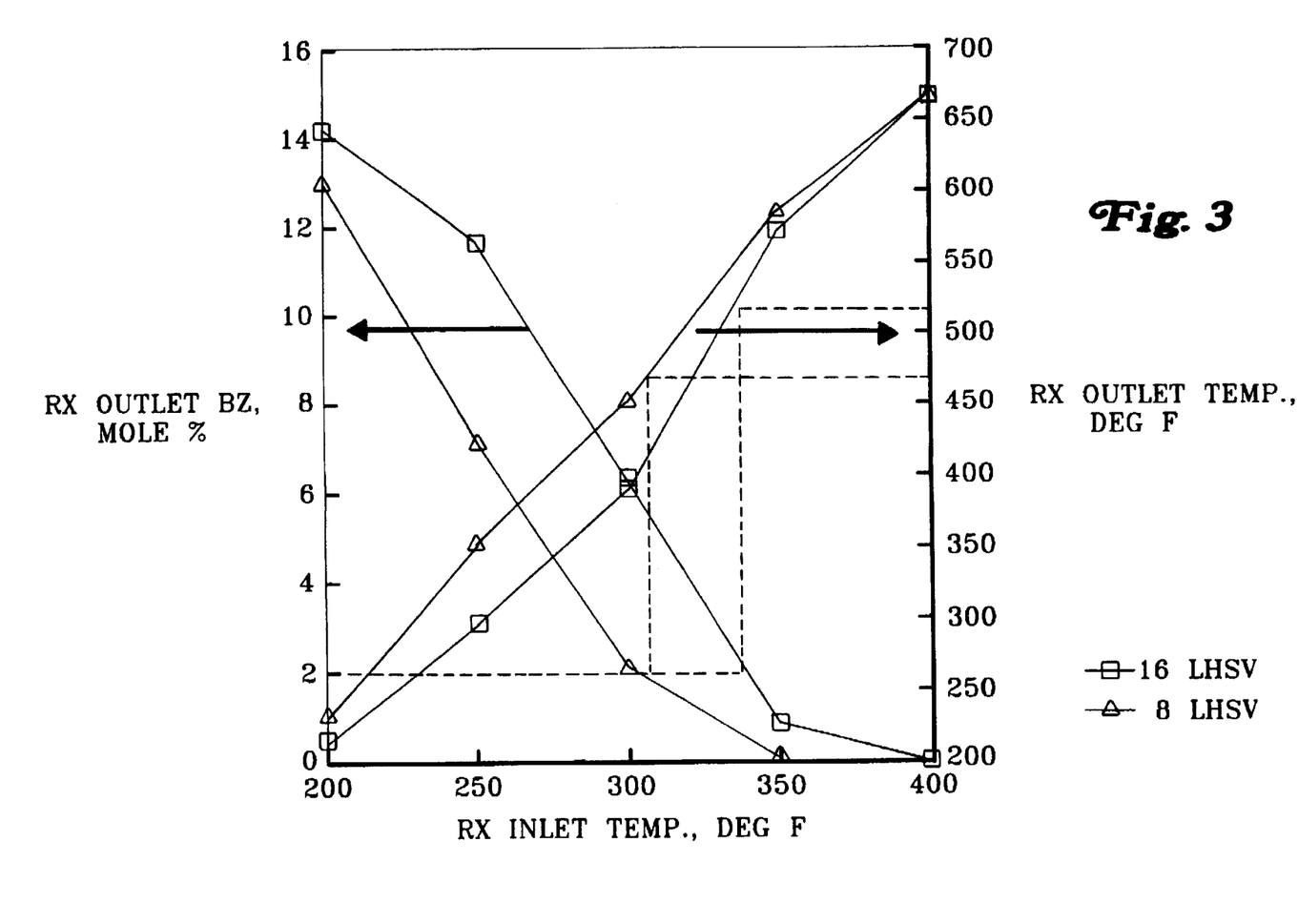
Figure 4:
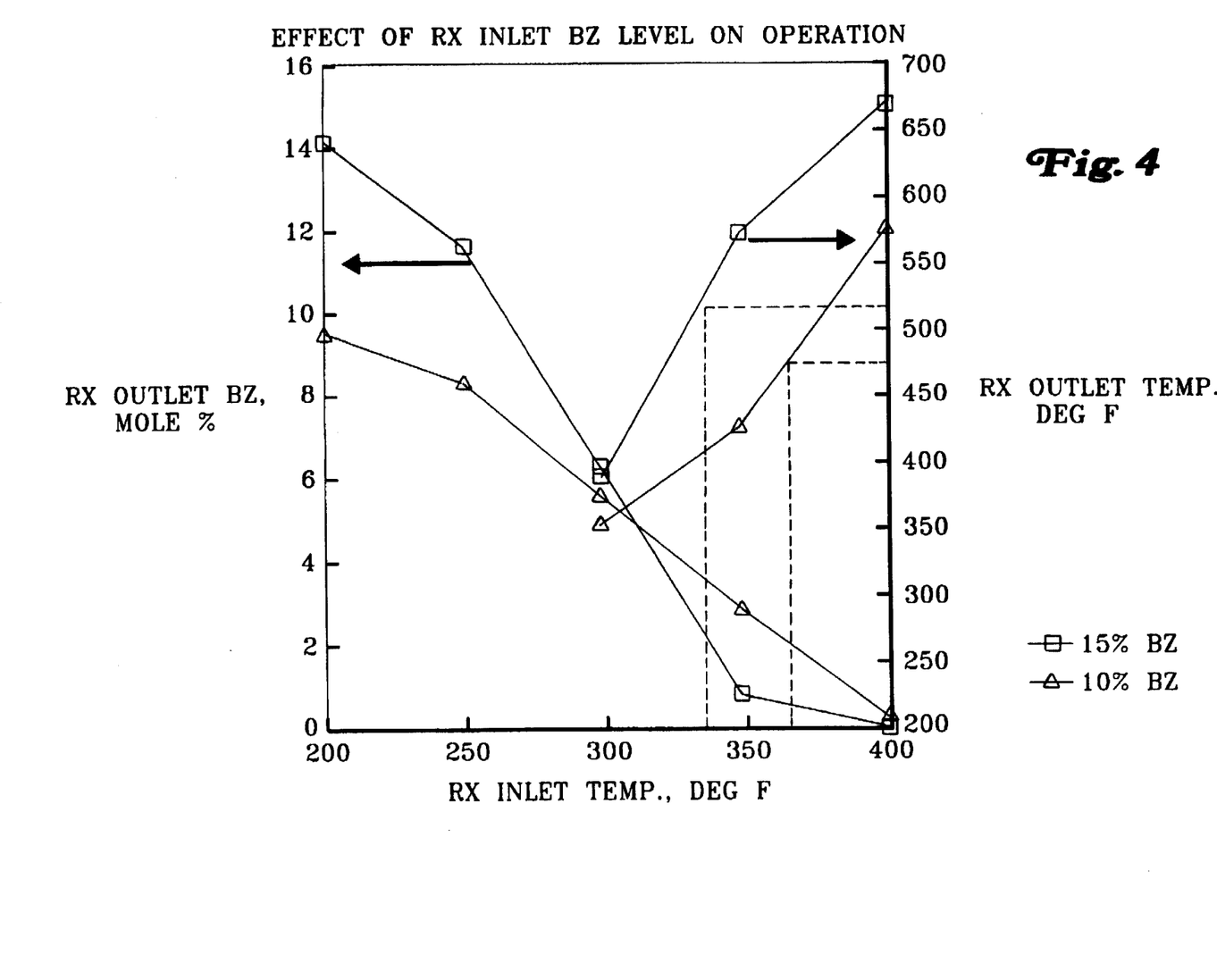

A kinetic model was developed to fit data collected from the series of pilot experiments. These data show for a mixed phase saturation reactor the importance that maintaining a benzene saturation reactor outlet temperature above 480° F. has on producing a saturation effluent with an outlet concentration benzene concentration below about 2 mol %. FIG. 2 shows the effect of variations in operating pressure on the benzene concentration of the reactor outlet as a function of reactor outlet temperature. Starting at 2 mol % on the left vertical scale and moving horizontally to the right, the intersection of the 2 mol % value with left side scale curves shows that inlet temperatures of about 310° F. and 360° F., respectively, correspond to the 2 mol % benzene outlet concentration for 450 and 250 psig, respectively. Moving upwardly from these values of inlet temperatures the corresponding outlet temperatures read from the intersection of the right side scale curves are about 470° F. and 600° F., respectively. Reading FIG. 3 in the same manner shows that the necessary outlet reactor temperatures for a 2 mol % benzene outlet concentration corresponding to a 16 and an 8 LHSV are about 520° F. and 470° F., respectively. Finally, FIG. 4 demonstrates that the reactor outlet temperature must be maintained in a narrow temperature band of about 480° F. to about 580° F. to obtain a benzene concentration of less than 2 mol % in the outlet stream. Therefore, the production of less than 2 mol % benzene from a mixed phase benzene saturation reaction zone is achieved by maintaining a narrow band of outlet saturation temperatures in a range of from 480° F. to 600° F. Slightly higher temperatures than those predicted are used in actual operation to insure a sufficiently low benzene concentration in the reactor. Surprisingly, the necessary temperature for the saturation occurs in a relatively narrow band despite substantial changes in pressures, space velocities and feed benzene concentration.

TABLE 2

| COMPOSITION, MOLE 5% | |
|---|---|
| Iso-pentane | 13.77 |
| N-Pentane | 20.54 |
| Cyclo-Pentane | 2.01 |
| 2,2-DMB | 0.53 |
| 2,3-DMB | 1.27 |
| 2-MP | 10.80 |
| 3-MP | 7.62 |
| N-hexane | 19.26 |
| MCP | 12.71 |
| CH | 1.06 |
| Benzene | 10.00 |
| C7+ | 0.43 |
| TOTAL | 100.00 |
| MOLECULAR WEIGHT | 80.0185 |
| STD DENSITY, LB/FT3 | 42.7024 |

We claim:

1. A process for the saturation of benzene, said process comprising:

passing a feedstream comprising at least one of $C_5$ and $C_6$ paraffinic hydrocarbons and at least 10 mol % benzene to a guard bed for the removal of sulfur and recovering a guard bed effluent from said guard bed;

admixing a hydrogen containing stream in an amount regulated by a flow controller with the guard bed effluent to produce a combined feed;

contacting said combined feed in a benzene saturation zone with a benzene saturation catalyst comprising a platinum metal in an amount of 0.1 to 1 wt % on an alumina support having a surface area of from 160 to 200 $m^2/g$, at benzene saturation conditions including mixed phase conditions to produce a saturation effluent stream and heat said saturation effluent stream to a temperature in a range of from 480° F. to 600° F.;

withdrawing said saturation effluent stream from said benzene saturation zone at a temperature of from 480° F. to 600° F., said benzene saturation effluent containing not more than 2 mol % benzene and having a hydrogen/hydrocarbon ratio of less than 0.02; and, varying the amount of said hydrogen stream admixed with the effluent of said guard bed in response to the mount of hydrogen in said saturation effluent stream.

2. The process of claim 1 wherein said saturation effluent stream is cooled and passed to a saturation effluent stream receiver, said receiver is maintained at the bubble point of said saturation effluent stream, pressure in said receiver is sensed and the mount of said hydrogen stream admixed with the effluent of said guard bed is varied by a flow controller in response to the pressure in said receiver.

3. The process of claim 1 wherein said saturated effluent stream contains less than 0.01 mol % benzene.

4. The process of claim 1 wherein said saturation effluent is dried.

5. The process of claim 4 wherein said saturation effluent is combined with a dried hydrogen stream to provide a combined saturation effluent stream having a hydrogen to hydrocarbon ratio of from 0.04 to 2.

6. The process of claim 1 wherein a temperature sensor measures the saturation effluent stream temperature and a portion of said saturated effluent stream is passed to said benzene saturation reactor in response to the effluent temperature.

7. The process of claim 2 wherein a sensor measures the liquid level in said receiver and a flow controller adjusts the rate at which said saturation effluent exits said receiver.

8. The process of claim 1 wherein said saturation effluent has a temperature of from 500° to 550° F.

9. The process of claim 1 wherein said benzene saturation conditions include a pressure of from 300 to 500 psig.

10. The process of claim 1 wherein said benzene saturation conditions include a LHSV of from 4 to 12.

11. The process of claim 2 wherein said saturation effluent stream is cooled to a temperature of from 100° to 150° F.

12. The process of claim 6 wherein said portion of said saturation effluent stream enters said benzene saturation reactor when said saturation product stream temperature exceeds a temperature of 600° F.

13. The process of claim 1 wherein said feedstream contains at least 15 mol % benzene.

14. A process for the saturation of benzene and the isomerization of hydrocarbons, said process comprising:

passing a feedstream comprising at least one of a $C_5$–$C_6$ paraffinic hydrocarbon and at least 10 mol % benzene to a guard bed for the removal of sulfur;

splitting a hydrogen rich stream into a first hydrogen stream and a second hydrogen stream;

drying said first hydrogen stream in a drier to produce a dried hydrogen stream;

admixing said feedstream from said guard bed with said second hydrogen stream in an amount regulated by a flow controller to produce a combined feed;

contacting said combined feed in a benzene saturation zone with a benzene saturation catalyst comprising platinum metal in an amount of 0.1 to 1 wt % on an alumina support having a surface of from 160 to 200 $m^2/g$ at benzene saturation conditions including mixed phase conditions;

withdrawing a saturation effluent stream from said benzene saturation zone at a temperature of from 480° F. to 600° F., said benzene saturation effluent containing not more than 2 mol % benzene;

cooling said saturation zone effluent stream and passing said saturation zone effluent stream to a receiver;

maintaining said receiver at the bubble point of said saturation zone effluent stream and sensing the pressure in said receiver;

adjusting the amount of said second hydrogen stream admixing with the effluent of said guard bed by said flow controller in response to the pressure in said receiver;

recovering a saturated effluent stream from said receiver, drying said saturated effluent stream and combining the dried saturated effluent stream with said first hydrogen stream to produce an isomerization stream;

passing said isomerization zone feed stream to an isomerization reactor and contacting said isomerization zone feed stream with an isomerization catalyst at isomerization conditions; and, recovering an isomerization zone product stream from said isomerization reaction zone.

15. The process of claim 14 wherein said isomerization zone feed stream has a hydrogen to hydrocarbon ratio of at least 0.04.

16. The process of claim 14 wherein said receiver contains less than 2 mol % hydrogen and said first hydrogen stream supplies at least 50% of the hydrogen in said isomerization zone feed stream.

17. The process of claim 14 wherein said saturation zone effluent stream has a hydrogen concentration of less than 0.01 mol %.

18. The process of claim 14 wherein a temperature sensor measures the effluent temperature of said saturation zone effluent stream before cooling of said saturation effluent stream and a potion of said saturation effluent stream is at least intermittently passed to said benzene saturation reactor in response to the effluent temperature.

19. The process of claim 14 wherein a sensor measures the liquid level in said receiver and a flow controller adjusts the rate at which said saturation effluent stream exits said receiver.

20. The process of claim 14 wherein said saturation zone effluent stream is cooled to a temperature of from 100° to 150° F.

21. The process of claim 14 wherein said portion of said saturation zone effluent stream has a temperature in a range of from 500° F. to 550° F.

* * * * *

UNITED STATES PATENT AND TRADEMARK OFFICE
CERTIFICATE OF CORRECTION

PATENT NO. : 5,663,466
DATED : September 2, 1997
INVENTOR(S) : LYNN H. RICE and DONALD H. BELL It is certified that error appears in the above-identified patent and that said Letters Patent is hereby corrected as shown below:

In column 13, line 26, the word "mount" should be "amount".

Signed and Sealed this

Second Day of December, 1997

Attest:

BRUCE LEHMAN

Attesting Officer

Commissioner of Patents and Trademarks